(12) United States Patent
Rossi

(10) Patent No.: US 8,778,884 B2
(45) Date of Patent: Jul. 15, 2014

(54) GLIOPROTECTANT PEPTIDE FOR USE IN THE TREATMENT OF AMYOTROPHIC LATERAL SCLEROSIS (ALS) AND METHODS RELATED THERETO

(75) Inventor: Daniela Maria Carmelita Rossi, Milan (IT)

(73) Assignee: Fondazione Salvatore Maugeri Clinica del Lavora e Della Riabilitazione, Pavia (IT)

( * ) Notice: Subject to any disclaimer, the term of this patent is extended or adjusted under 35 U.S.C. 154(b) by 0 days.

(21) Appl. No.: 13/479,506

(22) Filed: May 24, 2012

(65) Prior Publication Data

US 2012/0309687 A1 Dec. 6, 2012

Related U.S. Application Data

(60) Provisional application No. 61/490,252, filed on May 26, 2011.

(51) Int. Cl.
*A61P 25/00* (2006.01)
*A61P 25/28* (2006.01)
*A61K 38/16* (2006.01)

(52) U.S. Cl.
USPC .................. 514/17.7; 514/18.9; 514/21.3

(58) Field of Classification Search
None
See application file for complete search history.

(56) References Cited

U.S. PATENT DOCUMENTS

2006/0166881 A1* 7/2006 Hotchkiss et al. .............. 514/12

OTHER PUBLICATIONS

Brabant et al. (Apoptosis 14: 1190-1203, 2009).*
Tsujimoto (Catecholamine Res, Edit. Nagatsu et al. pp. 249-252, 2002).*
Seifert et al. Nature 7: 194-206, 2006.*
Shimuzu et al PNAS 97: 3100-3105, 2000.*
Martorana et al., "The BH4 Domain of Bcl-$X_L$ Rescues Astrocyte Degeneration in Amyotrophic Lateral Sclerosis by Modulating Intracellular Calcium Signals," Hum. Mol. Genet. 21:826-840, 2012.

* cited by examiner

*Primary Examiner* — Daniel E Kolker
*Assistant Examiner* — Aditi Dutt
(74) *Attorney, Agent, or Firm* — Clark & Elbing LLP

(57) ABSTRACT

The described invention relates to the use of the TAT-BH4 peptide for treating or preventing the progression of ALS. The methods include, postponing the appearance of symptoms and improving motor performance and survival in ALS. Methods are also provided, wherein the TAT-BH4 peptide is in a composition further comprising a pharmaceutically acceptable excipient.

14 Claims, 12 Drawing Sheets

Figure 1 C-D
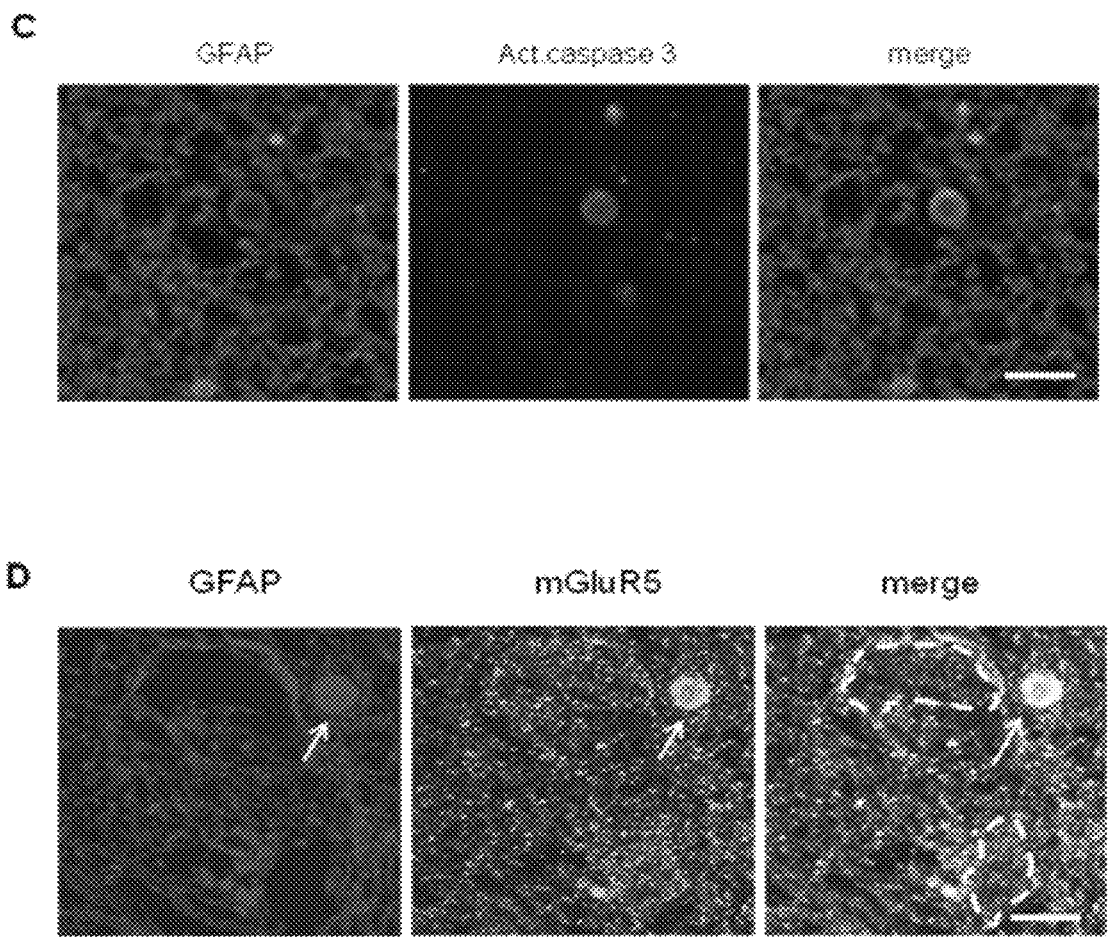

Figure 2 B -D
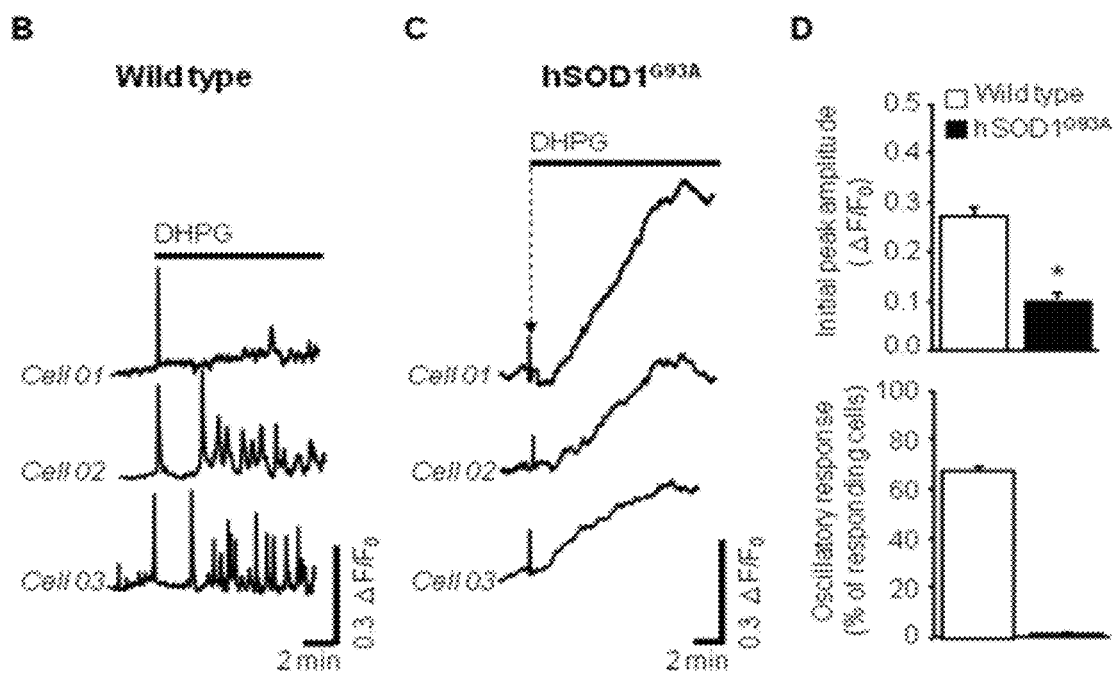

Figure 3 C - D
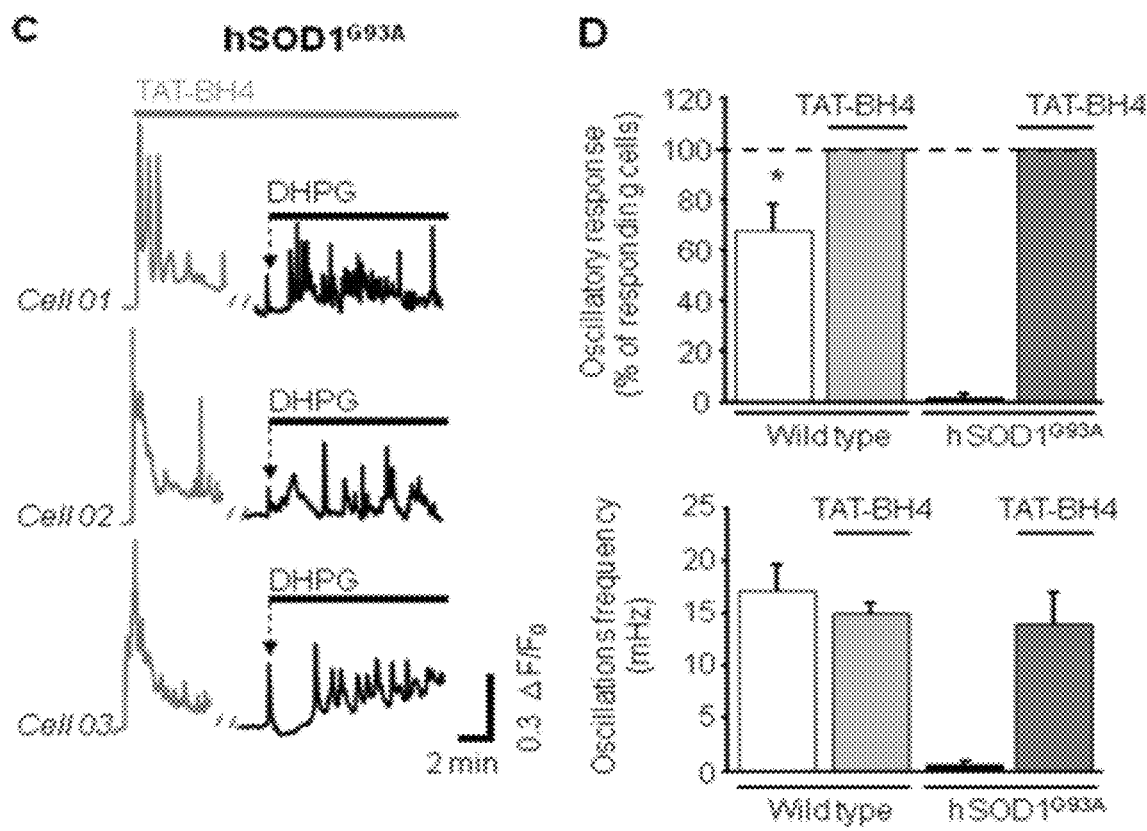

Figure 4 A - B
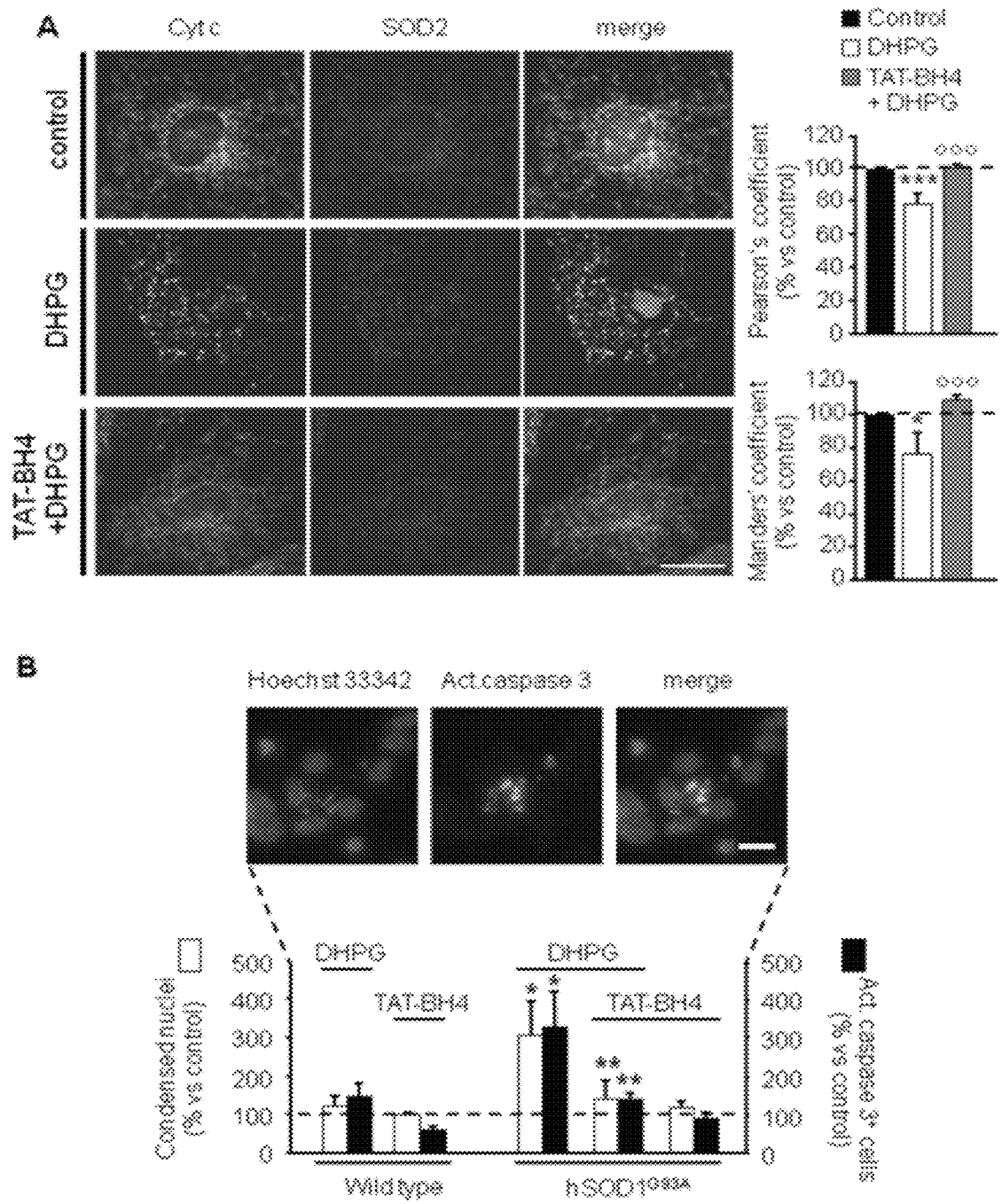

Figure 4 C - E
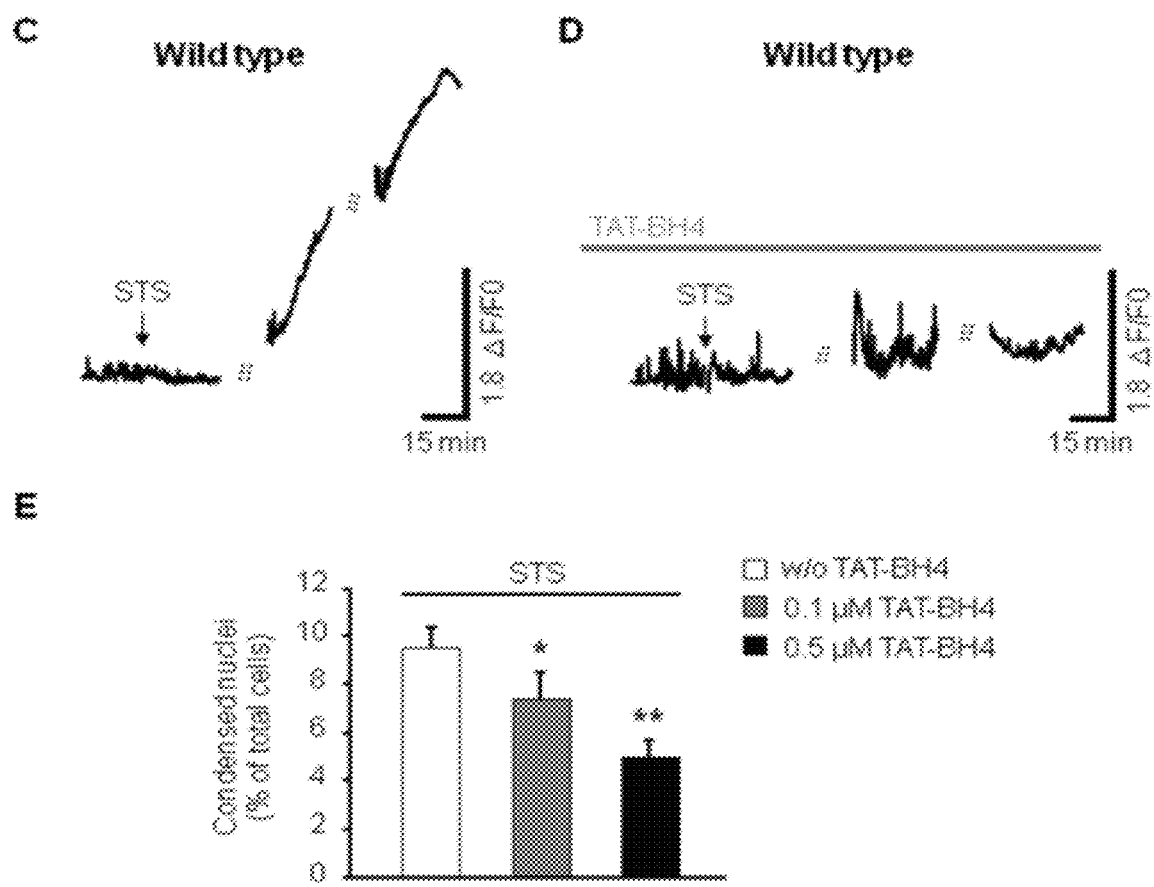

Figure 5 A - C
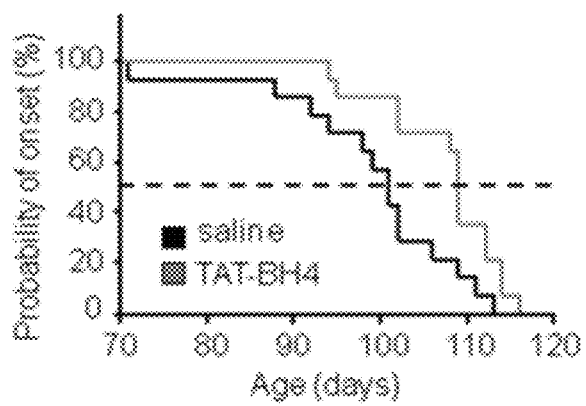
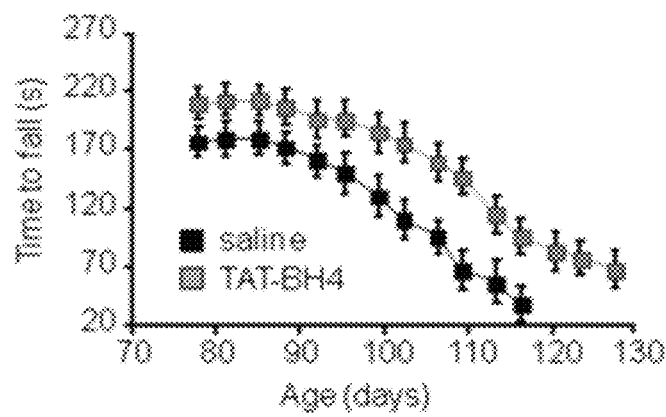
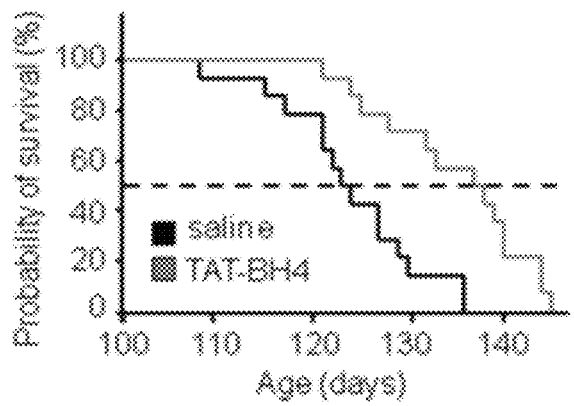

Figure 5 D - E
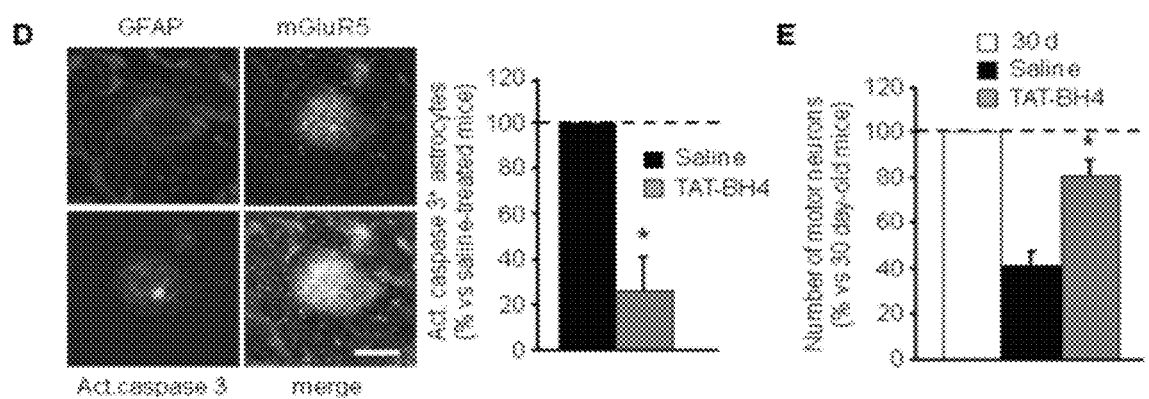

```
                        SEQUENCE LISTING

<160> NUMBER OF SEQ ID NOS: 5

<210> SEQ ID NO 1
<211> LENGTH: 32
<212> TYPE: PRT
<213> ORGANISM: artificial sequence
<220> FEATURE:
<223> OTHER INFORMATION: Human immunodeficiency virus (HIV) TAT protein
      (amino acids 1-10), linker (amino acids 11-12) and homo sapiens or
      mus musculus (amino acids 13-32)

<400> SEQUENCE: 1

Gly Arg Lys Lys Arg Arg Gln Arg Arg Arg Gly Gly Ser Asn Arg Glu
1               5                   10                  15

Leu Val Val Asp Phe Leu Ser Tyr Lys Leu Ser Gln Lys Gly Tyr Ser
            20                  25                  30

<210> SEQ ID NO 2
<211> LENGTH: 19
<212> TYPE: DNA
<213> ORGANISM: Mus musculus
<220> FEATURE:
<221> NAME/KEY: misc_feature
<222> LOCATION: (1)..(19)
<223> OTHER INFORMATION: 5' mGluR5-Car primer

<400> SEQUENCE: 2
agctgttttg tccacatat                                                      19

<210> SEQ ID NO 3
<211> LENGTH: 19
<212> TYPE: DNA
<213> ORGANISM: Mus musculus
<220> FEATURE:
<221> NAME/KEY: misc-feature
<222> LOCATION: (1)..(19)
<223> OTHER INFORMATION: 3'-mGluR5- Car primer

<400> SEQUENCE: 3
ccagagagtg ttgagttag                                                      19

<210> SEQ ID NO 4
<211> LENGTH: 21
<212> TYPE: DNA
<213> ORGANISM: Mus musculus
<220> FEATURE:
<221> NAME/KEY: misc_feature
<222> LOCATION: (1)..(21)
<223> OTHER INFORMATION: 5'-HPRT primer
```

-continued

```
<400> SEQUENCE: 4
tgaatcacgt ttgtgtcatt a                                              21

<210> SEQ ID NO 5
<211> LENGTH: 21
<212> TYPE: DNA
<213> ORGANISM: Mus musculus
<220> FEATURE:
<221> NAME/KEY: misc_feature
<222> LOCATION: (1)..(21)
<223> OTHER INFORMATION: 3?-HPRT primer
<220> FEATURE:
<221> NAME/KEY: misc_feature
<222> LOCATION: (1)..(21)
<223> OTHER INFORMATION: 3'-HPRT primer

<400> SEQUENCE: 5
ttcaacttgc gctcatctta g                                              21
```

GLIOPROTECTANT PEPTIDE FOR USE IN THE TREATMENT OF AMYOTROPHIC LATERAL SCLEROSIS (ALS) AND METHODS RELATED THERETO

CROSS-REFERENCE TO RELATED APPLICATIONS

This application claims the benefit of U.S. Provisional Application No. 61/490,252, filed on May 26, 2011, the contents of which are hereby incorporated by reference in their entirety.

The application is file within the grace period from the following publication: Martorana F, et. Al; Hum Mol Genet. 2012 Feb. 15; 21(4):826-40. Epub 2011 Nov. 9. "The BH4 domain of Bcl-$X_L$ rescues astrocyte degeneration in amyotrophic lateral sclerosis by modulating intracellular calcium signals."

REFERENCE TO A SEQUENCE LISTING SUBMITTED AS A TEXT FILE

The official copy of the sequence listing is filed concurrently with the specification. The sequence listing is part of the specification and is herein incorporated by reference in its entirety.

FIELD OF THE INVENTION

The described invention relates to the use of the TAT-BH4 peptide for treating or preventing the progression of ALS.

BACKGROUND OF THE INVENTION

Amyotrophic Lateral Sclerosis (ALS) is a neurodegenerative disorder characterized by the progressive degeneration of corticospinal and spinal motor neurons. Most cases are sporadic (sALS), but about 5-10% of patients have an inherited familial form of the disease. About one-fifth of these is linked to mutations in the gene coding for the SOD1 protein. Transgenic animals carrying single-amino acid mutations of human SOD1 develop progressive motor neuron disease that recapitulates in many aspects the human pathology. The cascade of events ultimately responsible for motor neuron degeneration, however, remains elusive. Recent observations suggest that a complex pathological interplay subsists between motor neurons and the neighboring glial cells.

In the adult nervous system, the major glial cell type is represented by the astrocytes. These cells fulfill several homeostatic functions that collectively contribute to maintain the optimal microenvironment for neuronal function and survival. In addition, astroglial cells can sense neuronal activity by means of a wide array of neurotransmitter receptors located in their plasma membrane and, in turn, they can respond to neurons by $Ca^{2+}$-dependent release of gliotransmitters. The multiplicity and complexity of these activities clearly indicates that the correct performance of the astrocytes is crucial for the physiological functioning of the nervous system, and its derangement may affect neuronal activity and contribute to neurodegeneration.

A crucial indication that astrocyte alterations are implicated in ALS progression in vivo came from the observations that reducing mutant SOD1 expression within astrocytes significantly affected the progression of the disease in transgenic mice. In keeping, ALS-linked mutant SOD1-expressing astroglial cells in culture were reported to secrete factors that are toxic to motor neurons. Furthermore, in both ALS patients and transgenic animals, there is evidence for biochemical and functional alterations of the astrocytes. Within this framework, a degenerative process of the astrocytes, positioned in the microenvironment of motor neurons, was reported in the spinal cord of transgenic mice over-expressing the mutant human $SOD1^{G93A}$ ($hSOD1^{G93A}$) protein. This phenomenon occurs prior to symptom onset and is mediated by the excitatory amino acid glutamate via the activation of its inositol 1,4,5 triphosphate ($IP_3$)-producing metabotropic receptor type-5 (mGluR5). Consistent evidence indicates that the physiological production of $IP_3$, under the stimulation of cell-surface receptors, such as mGluR5, normally triggers the release of $Ca^{2+}$ from the endoplasmic reticulum (ER) by opening the $IP_3$ receptor ($IP_3R$) channels.

Such $Ca^{2+}$ plays a role in modulating a variety of cellular responses that are fundamental for cell function and survival. However, $Ca^{2+}$ released under non-physiological conditions can activate different pathways of cell death.

It follows that the identification of pharmacological agents that modulate the release of $Ca^{2+}$ from the ER may be relevant to prevent astroglial cell death in ALS, and thus contribute to overcome the symptoms and manifestations of the disease.

SUMMARY OF THE INVENTION

The present invention concerns a method for treating or preventing the progression of ALS. The method comprises the administration of a TAT-BH4 peptide to a subject in need thereof.

DESCRIPTION OF THE FIGURES

FIG. 4. Glioprotective effect of the TAT-BH4 peptide against DHPG and staurosporine toxicity. (A, B) Astrocyte cultures from wild-type or hSOD1$^{G93A}$ mice were pre-treated in the absence or presence of 0.5 μM TAT-BH4 for 30 min and then incubated with 100 μM DHPG. (A) Representative images of hSOD1$^{G93A}$-expressing astrocytes double-immunolabeled for cytochrome c (Cyt c, left panels) and the mitochondrial marker manganese superoxide dismutase (SOD2, middle panels); nuclei were stained with Hoechst 33342. Scale bar, 20 μm. Note that the treatment with DHPG causes mitochondrial disarrangement and release of cytochrome c, as revealed by the loss of co-localization between Cyt c and SOD2 immunosignals. Pre-treatment with TAT-BH4 restores the complete co-localization of the two proteins, similar to the situation in control conditions. Histograms show the mean Pearson's and Manders' coefficients as calculated using JACoP plug-in of ImageJ software in the different experimental conditions. Data (mean±s.e.m.) are expressed as percentage of Pearson's and Manders' coefficients of control condition (control values: Pearson's coefficient: 0.864±0.008; Manders' coefficient (M2): 0.728±0.016, n=25 cells for each experimental condition) (*p<0.05 and ***p<0.0001 vs control, °°°p<0.0001 vs DHPG, one-way ANOVA followed by Bonferroni post-hoc test). (B) Treatment with DHPG induces an increment in the percentage of hSOD1$^{G93A}$-expressing astrocytes with nuclear condensation and caspase-3 activation as compared with wild-type cells. Data (mean±s.e.m.) are expressed as % of control, i.e. the corresponding culture type challenged with saline (control values: cells with condensed nuclei: wild-type: 0.96±0.07%; hSOD1$^{G93A}$: 0.98±0.13%; cells immunopositive for active caspase-3: wild-type: 0.32±0.08%; hSOD1$^{G93A}$: 0.33±0.07%, n=3 in triplicate. The presence of TAT-BH4 significantly reduced the percentage of ALS astrocytes showing nuclear condensation and caspase-3 activation. (*p<0.05 vs control; **p<0.05 vs DHPG, one-way ANOVA followed by Bonferroni post-hoc test). Above the histograms, representative images of astrocytes with condensed nuclei (Hoechst 33342) and immunopositive for the active caspase 3. Scale bar, 20 μm. (C-D) The TAT-BH4 peptide restores normal [Ca$^{2+}$]$_i$ signalling in staurosporine (STS)-treated wild-type astrocytes in culture. (C) Typical single cell [Ca$^{2+}$]$_i$ response of wild-type astrocytes to application of 1 μM STS. Note that the majority of cells (n=81 cells analyzed; n=5 experiments) responded with an abnormal long-lasting calcium rise that reaches the plateau in about 75-80 min. (ΔF/F$_0$ 3.52±0.22). (D) Representative single cell [Ca$^{2+}$]$_i$ transients obtained in wild-type astrocytes treated with TAT-BH4 peptide (0.5 μM) for 30 min. before the local application of STS (1 μM; black trace). Note that TAT-BH4 reduced the persistent [Ca$^{2+}$]$_i$ rise evoked by STS (−72%; n=76 cells analyzed; n=5 experiments) and restored [Ca$^{2+}$]$_i$ oscillations. (E) Astrocyte cultures were pre-incubated for 30 min. in the absence (w/o TAT-BH4) or in the presence of increasing concentrations of TAT-BH4 (0.1 or 0.5 μM), and then treated with STS (1 μM) for 6 h. The latter caused an increment in the percentage of cells with nuclear condensation whereas the peptide reduced the number of apoptotic cells in a dose-dependent manner. Data (mean±s.e.m.) are expressed as % of total cells (n=3 in duplicate, *p<0.05 and **p<0.01 vs staurosporine w/o TAT-BH4, one-way ANOVA followed by Bonferroni post-hoc test).

FIG. 5. Treatment of hSOD1$^{G93A}$ mice with the TAT-BH4 peptide alleviates the manifestations of the disease. (A) Kaplan-Meier curves represent the ages at which disease onset (peak body weight) was reached for saline- and TAT-BH4-treated (TAT-BH4, 5 mg/kg i.p. daily) hSOD1$^{G93A}$ mice (n=14 mice for each condition). Note that the onset of symptoms in TAT-BH4-treated mice is significantly retarded by 8 days compared to controls (p<0.05; Logrank test). (B) Rotarod performance of transgenic hSOD1$^{G93A}$ mice treated with saline or TAT-BH4 (n=14 mice for each condition). TAT-BH4 significantly improves motor performance in hSOD1$^{G93A}$ mice when compared to saline-treated animals. Data (mean±s.e.m.) are expressed as the average time of permanence on the rod of all animals (p<0.05; repeated measures ANOVA). (C) Survival analysis of saline- and TAT-BH4-treated hSOD1$^{G93A}$ mice (n=14 mice for each condition). The life span TAT-BH4-treated mice is significantly extended of 15 days (p<0.05; Logrank test). The dotted lines in A and C indicate the median values in the two mouse populations. (D) Representative images of a degenerating astrocyte as defined by GFAP (top, left panel) and showing active caspase 3 (bottom, left panel) and mGluR5 (top, right panel) immunoreactivity. Scale bar, 10 µm. Histograms indicate the percentage of spheroid astrocytes that are positive for the active caspase 3 in sections from 100 day-old saline- or TAT-BH4-treated hSOD1$^{G93A}$ mice (n=3 mice for each condition). Data (mean±s.e.m.) are expressed as % of total active caspase 3-positive spheroid astrocytes present in 100 day-old saline-treated hSOD1$^{G93A}$ mice (46±16 active-caspase 3-positive astrocytes). The number of caspase-3-positive cells is significantly lower in the TAT-BH4-treated group. (*p<0.05 vs saline, unpaired t-test). (E) Histograms show the number of motor neurons in spinal cord sections from 30 day-old untreated hSOD1$^{G93A}$ animals or 100-day-old saline- or TAT-BH4-treated hSOD1$^{G93A}$ mice (n=3 mice for each condition). Data (mean±s.e.m.) are expressed as % of total motor neurons present in 30 day-old untreated hSOD1$^{G93A}$ mice (596.1±96.14; *p<0.05 vs saline, one-way ANOVA followed by Bonferroni post-hoc test).

Figure 1:
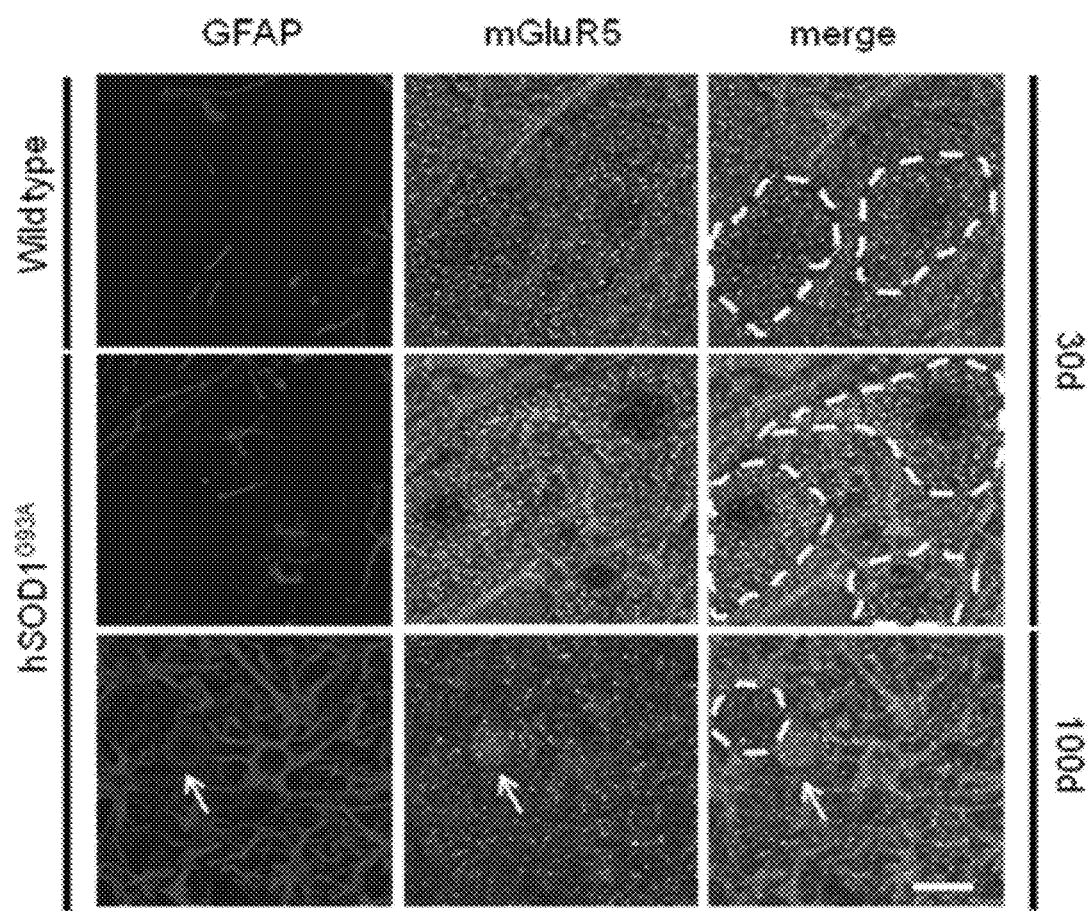
FIG. 1. Distribution and expression of mGluR5 in the spinal cord of $hSOD1^{G93A}$ mice and sporadic ALS patients. (A) Representative images of lumbar spinal cord sections from 30 day-old wild-type and pre-symptomatic $hSOD1^{G93A}$ animals (30d) or 100 day-old symptomatic $hSOD1^{G93A}$ mice (100d). Sections were double immunostained for GFAP (gray filamentous staining) and mGluR5 (bright dots) to visualize astrocytic cytoskeleton and metabotropic glutamate receptor clusters, respectively. Arrows indicate degenerating astroglial cells and dotted lines outline motor neuronal cell bodies. Scale bar, 20 μm. (B) Expression of mGluR5 was determined by quantitative reverse transcription-polymerase chain reaction (qRT-PCR) analysis on total RNA from 30 (30d) and 100 day-old (100d) wild-type and $hSOD1^{G93A}$ spinal cords (n=3 mice per age and genotype). Values (mean±s.e.m.) were normalised relative to the housekeeping gene hypoxanthine guanine phosphoribosyl transferase (HPRT) and expressed as percentage of mGluR5 expression levels in 30 day-old wild-type mice (*$p<0.05$ vs 30 day-old $hSOD1^{G93A}$ mice, **$p<0.01$ vs 30 day-old wild-type mice, two-way ANOVA followed by Bonferroni post-hoc test). (C) Degenerating astroglial cells are present in the spinal cord of autoptic sALS cases. Representative images of a degenerating astrocyte with the typical spheroidal cap of GFAP (left panel) and immunopositive for the active caspase 3 (middle panel). Scale bar, 20 μM. (D) Typical images of human post-mortem ALS spinal cord sections double immunolabeled with antibodies against GFAP (left panel) to mark the astrocytic cytoskeleton, and mGluR5 (middle panel), to visualize the metabotropic glutamate receptor puncta. (A-B) Arrows indicate degenerating astroglial cells and dotted lines outline motor neuronal cell bodies. Scale bar, 20 μm.
Figure 1:
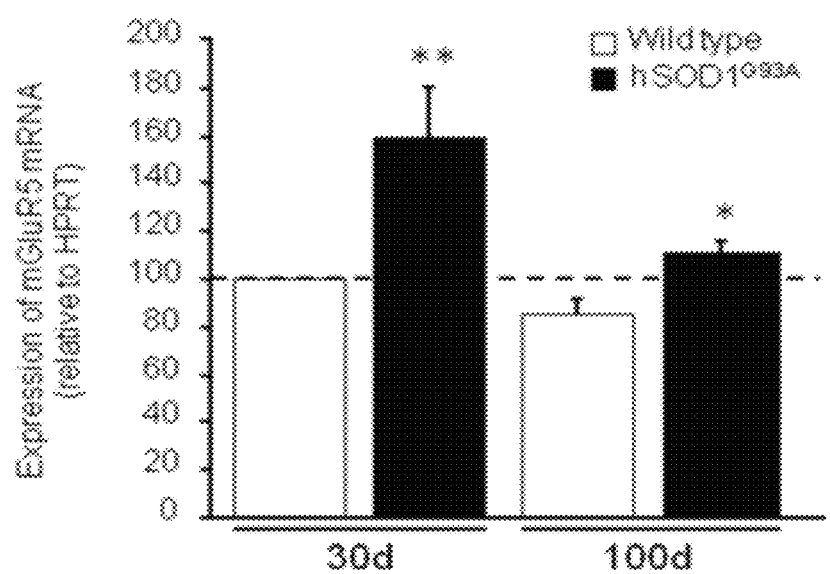

The invention will become more fully clear from the following detailed description, given by way of a mere exemplifying and non limiting examples, to be read with reference to the attached drawing figures.

DETAILED DESCRIPTION OF THE INVENTION

The described invention provides methods and compositions utilizing a TAT-BH4 peptide for treating or preventing the progression of ALS.

The increasing knowledge of astrocyte physiology has lately challenged the traditional neuron-centric vision of brain disorders and raised more questions about the role of astroglia in various neurodegenerative diseases. Consistent with this view, a significant number of recent observations has indicated that, in ALS, degeneration of motor neurons is non-cell-autonomous. Rather, it requires combined alterations in motor neurons and the surrounding non-neuronal cells, including the astrocytes. Within this perspective, a degenerative process of the astrocytes, located in the neighborhood of motor neurons, was identified in the spinal cord of hSOD1$^{G93A}$ ALS transgenic mice. Since astrocytes constitute the principal element of the brain homeostatic system, being responsible for all aspects of metabolic support, nutrition, control of ion and transmitter environment, regulation of brain-blood barrier and defense of the CNS, it is highly likely that their loss will deprive the adjacent motor neurons of the optimal microenvironment, thus exacerbating both their degeneration and the disease progression. Therefore, the pharmacological protection of astrocytes represents an innovative approach to positively impact the course of ALS disease.

According to one aspect, the described invention provides a method for treating or preventing the progression of ALS by administering a therapeutically effective amount of a TAT-BH4 peptide to a subject in need thereof, thereby treating or preventing at least one manifestation or symptom of ALS. Early manifestations and symptoms of ALS can be quite varied among individuals, but usually include tripping, dropping things, abnormal fatigue of the arms and/or legs, slurred speech, muscle cramps and twitches and/or uncontrollable periods of laughing or crying. The hands and feet may be affected first, causing difficulty in lifting, walking or using the hands for the activities of daily living such as dressing, washing and buttoning clothes. As the disease progresses, weakening and paralysis continue to spread to the muscles of the trunk, eventually affecting speech, swallowing, chewing and breathing. Since ALS attacks only motor neurons, but not other neuronal cell types, the sense of sight, touch, hearing, taste and smell are not affected. For many people, muscles of the eyes and bladder are generally not affected.

According to a further aspect, the invention provides a method for treating or preventing the progression of ALS by administering a therapeutically effective amount of a TAT-BH4 peptide to a subject in need thereof, wherein the TAT-BH4 peptide comprises the BH4 domain of Bcl-X$_L$ (amino acids 13-32 of the TAT-BH4 peptide: SNRELVVDFL-SYKLSQKGYS) which is homologous in both homo sapiens and mus musculus and the protein transduction domain of the human immunodeficiency virus (HIV) TAT protein (amino acids 1-10 of the TAT-BH4 peptide: GRKKRRQRRR) and wherein the TAT-BH4 peptide has an amino acid sequence set forth in SEQ ID NO: 1 SEQ ID NO: 1 H$_2$N-GRKKRRQR-RRGGSNRELVVDFLSYKLSQKGYS-COOH Amino acids 11-12 of the TAT-BH4 peptide (GG) link the protein transduction domain of the human immunodeficiency virus (HIV) TAT protein to the BH4 domain of Bcl-X$_L$.

The anti-apoptotic activity of Bcl-2 family members, particularly Bcl-2 and Bcl-X$_L$, were reported, and were seen to confer cell death protection by altering the Ca$^{2+}$ permeability of the IP$_3$R channels. The anti-apoptotic activity of these proteins has been mostly ascribed to their homology domain 4 (BH4), and the one from Bcl-X$_L$ appears to be more efficient than that of Bcl-2.

It has been surprisingly found that the sole BH4 domain of Bcl-X$_L$, fused to the protein transduction domain of the HIV-1 TAT protein (TAT-BH4), is sufficient to restore sustained Ca$^{2+}$ oscillations and cell death resistance in astrocytes that express the enzyme superoxide dismutase 1 (SOD1) with mutations (G93A) that are linked to human ALS cases. Moreover it has been seen that the chronic treatment of ALS transgenic mice (hSOD1$^{G93A}$) with the TAT-BH4 peptide reduces focal degeneration of astrocytes, slightly postpones the disease onset and improves motor performance and survival of hSOD1$^{G93A}$ mice. These results point at TAT-BH4 as a novel glioprotective agent with a therapeutic potential for ALS. According to a further aspect, the described invention provides a method for treating or preventing the progression of ALS by administering a therapeutically effective amount of a TAT-BH4 peptide to a subject in need thereof, thereby treating or preventing at least one manifestation or symptom of ALS chosen from the group comprising twitching, cramping, stiffness or weakness of muscles, exaggerated reflexes, impaired speech and difficulty in chewing or swallowing. According to a still further aspect, the invention provides a method for treating or preventing the progression of ALS by administering a therapeutically effective amount of a TAT-BH4 peptide, wherein the TAT-BH4 peptide promotes cell-death resistance.

The cells that resist cell-death are chosen from the group consisting of astroglial cells and motor neurons.

According to a still further aspect, the invention provides a method for the treatment or prevention of the progression of ALS, wherein the TAT-BH4 peptide enhances cell survival by restoring Ca$^{2+}$ oscillations. Preferably said cells are spinal cord astrocytes and the intracellular Ca$^{2+}$ variations are controlled by the modulation of the IP$_3$ receptors.

Compelling evidence indicates that non-physiological release of Ca$^{2+}$ from the ER, in response to IP$_3$ production under the stimulation of cell surface receptors, may result in the activation of a wide variety of $Ca^{2+}$-dependent enzymes, which can recruit mitochondria to the apoptotic cascade or activate other cell death effectors. In normal astrocytes, the activation of group I mGluRs, including mGluR5, triggers the formation of $IP_3$ and the consequent release of $Ca^{2+}$ from the ER, resulting in intracellular calcium oscillations. However, in hSOD1$^{G93A}$-expressing astrocytes, stimulation with DHPG, a selective agonist of the group I mGluRs, does not produce calcium spiking, but causes in about 99% of the cells a persistent $[Ca^{2+}]_i$ rise, which is exceptionally elevated in a number of cells.

Since the function of the ER is intimately connected with that of mitochondria, during normal signaling, there is a continuous flow of $Ca^{2+}$ between the two organelles, which is relevant for the mitochondrial metabolic activity. However, alterations in $Ca^{2+}$ homeostatic mechanisms that result in massive and/or prolonged mitochondrial $[Ca^{2+}]_i$ overload can cause the release of cytochrome c, located between the inner and the outer mitochondrial membranes. This event can lead to the activation of cell death effector caspases. Consistently, the unusual efflux of intracellular $Ca^{2+}$ detected in the mutant SOD1-expressing cells, in combination with the loss of $IP_3R$-dependent $[Ca^{2+}]_i$ oscillations, correlates with the release of cytochrome c from mitochondria and the degeneration of ALS astrocytes.

It was surprisingly found that TAT-BH4 restores pro-survival $Ca^{2+}$ oscillations in astrocytes that express a mutant form of SOD1 linked to familial ALS cases and protects the cells from excitotoxic damage. Other apoptotic stimuli, such as staurosporine (STS), were reported to lead to cell death by disrupting the $IP_3$ receptor-mediated calcium homeostasis. In line with this, it was found that treating wild-type astrocytes with STS causes a sustained increase in $[Ca^{2+}]_i$, which is similar to that triggered by DHPG in ALS astrocytes, but to higher levels. Also in this case, the $[Ca^{2+}]_i$ rise is associated to degeneration of a significant number of cells. Interestingly, the $[Ca^{2+}]_i$ released by hSOD1$^{G93A}$-expressing or wild-type astrocytes treated with DHPG or STS, respectively, quantitatively correlates with the extent of cell death. Thus, it is thought to be the persistent release of $Ca^{2+}$ from the intracellular stores through the $IP_3Rs$ that underlies astrocyte degeneration. This finding is particularly interesting considering that $IP_3R2$, the isoform predominantly (or selectively) expressed in astrocytes, is up-regulated in cells from sporadic ALS patients.

Fine tuning of the intracellular $Ca^{2+}$ homeostasis by the anti-apoptotic Bcl-2/Bcl-$X_L$ proteins was described to control cell death mechanisms. While the BH4 domain of Bcl-2 was reported to be necessary and sufficient to prevent apoptosis by regulating the efflux of calcium from the ER, the role of the N-terminal BH4 domain of Bcl-$X_L$ in modulating pro-survival $Ca^{2+}$ signals was not explored. Thus, the impact of the BH4 domain of Bcl-$X_L$ on astrocyte $Ca^{2+}$ signalling by exploiting the biologically active TAT-BH4 peptide was investigated. The fact that TAT-BH4 re-establishes $Ca^{2+}$ oscillations and induces a significant reduction in the number of degenerating astrocytes in a dose-dependent manner upon staurosporine treatment, confirms the efficacy of the peptide towards $IP_3R$-dependent astroglial cell death, thus establishing a correlation between the deranged mGluR5 $Ca^{2+}$ signalling and the degenerative process of hSOD1$^{G93A}$-expressing astrocytes. According to a still further aspect, the invention provides a method for treating or preventing the progression of ALS by administering a therapeutically effective amount of a TAT-BH4 peptide, wherein the TAT-BH4 peptide post- pones the appearance of ALS symptoms, improves the motor performance and extends the life span in hSOD1$^{G93A}$ ALS transgenic mice.

Intraperitoneal injection of TAT-conjugated proteins was reported to allow an efficient transduction of the fusion proteins into the brain cells. In the present study, the therapeutic potential of TAT-BH4 in vivo by means of this route of administration was investigated. Dosages from 1 to 5 mg per kilogram of body weight were selected in preclinical trials for two reasons. First, the acute treatment of mice with an equivalent dose of TAT-Bcl-$X_L$ resulted protective against other neurodegenerative conditions, such as ischemic injury of the brain. Second, the chronic administration of such dose of TAT-conjugated proteins, on a daily basis, was reported to produce no signs of neurological impairment or systemic distress in wild-type mice, thus suggesting no obvious toxicity of the TAT protein. In hSOD1$^{G93A}$ mice, it was found that the prolonged treatment with the peptide, starting at the pre-symptomatic stage of the disease, slightly delays the onset of the disease and improves both motor performance and survival of ALS transgenic mice. These results surprisingly indicate for the first time the BH4 domain of Bcl-$X_L$ as a novel therapeutic for ALS.

Furthermore, this study points at cell-permeable peptides as an innovative class of drugs suitable for mechanistic studies and endowed with a potential for curing ALS.

In a still further aspect, the invention provides a method for treating or preventing the progression of ALS by administering a therapeutically effective amount of a TAT-BH4 peptide, wherein the TAT-BH4 peptide is a glioprotective agent.

It has surprisingly been found that TAT-BH4 plays an important role as a glioprotective agent in ALS.

In the current study, the observations made on the hSOD1$^{G93A}$ mouse model of familial ALS were further confirmed by analyzing post-mortem tissues from sporadic ALS patients. It was found that gliodegeneration is not only a peculiarity of the hSOD1$^{G93A}$ mice, but occurs also in the sporadic form of the human disease.

On a mechanistic standpoint, prior studies in vitro implied the involvement of mGluR5 in the event of astroglial damage. Consistent with a role for this receptor, it was further demonstrated that dying astrocytes are strongly immunoreactive for mGluR5 in the spinal cord of both symptomatic hSOD1$^{G93A}$ mice and autoptic sALS cases. The stage at which mGluR5 becomes relevant for ALS progression was subsequently investigated by determining the degree of the receptor expression in the spinal cord of hSOD1$^{G93A}$ ALS mice at different ages. Interestingly, it was found that the overall expression of mGluR5 was significantly enhanced in young, pre-symptomatic ALS animals when compared to both age-matched wild-type mice and symptomatic hSOD1$^{G93A}$ animals. However, at the time of disease onset, the amount of the receptor had generally declined to levels that are comparable to wild-type spinal cords. This strongly suggests that mGluR5 is likely to play a role in ALS progression during the early phases of the disease. Since the receptor was implicated in the degeneration of mutant SOD1-expressing astrocytes, particular attention was focused on these cells. Consistent with the data obtained on spinal cord tissue, neonatal astrocyte cultures, prepared from the spinal cord of hSOD1$^{G93A}$ mice, displayed increased expression of mGluR5 transcripts further confirming that the up-regulation of this receptor occurs during the early development also in ALS astroglia. Evidence indicates that activation of mGluR5 triggers degeneration of hSOD1$^{G93A}$-expressing astrocytes in vitro. In the current study, the authors confirm the excitotoxic damage of ALS astrocytes upon treatment with DHPG, a group I mGluR agonist. Because mGluR5 is the predominant group I mGluR in cultured astrocytes, besides being up-regulated in mutant SOD1-expressing cells, they ascribe the cytotoxic effect of DHPG to activation of this receptor. Further, it was demonstrated that pretreating the cells with TAT-BH4 protects hSOD1$^{G93A}$-expressing astrocytes from DHPG-dependent damage. In addition, in a preclinical trial with TAT-BH4, the authors confirm that the peptide reduces the number of astrocytes that express the apoptotic effector caspase-3 and preserves a greater number of motor neurons in vivo, in the hSOD1$^{G93A}$ mice. Whether the effect towards motor neurons is a consequence of the maintenance of a larger number of neuro-supportive astrocytes in the motor neuron microenvironment or can be partially ascribed to a direct action of the peptide on these cells remains to be elucidated.

According to a still further aspect, the invention provides a method for treating or preventing the progression of ALS by administering a therapeutically effective amount of a TAT-BH4 peptide, wherein the TAT-BH4 peptide is administered topically, subcutaneously, intramuscularly, or intravenously to a subject in need thereof in order to treat or prevent the progression of ALS.

Preferably the TAT-BH4 peptide is intraperitoneally administered. Any suitable route of administration may be used to deliver the TAT-BH4 peptide for the purposes of treating or preventing the progression of ALS. The term "administer" as used herein refers to the act of dispensing, supplying, applying, giving, or contributing to. The terms "administering" or "administration" are used interchangeably and include in vivo administration, as well as administration directly to tissue ex vivo. Administering can be performed, for example, once, a plurality of times, and/or over one or more extended periods.

In a preferred embodiment the TAT-BH4 peptide is chronically administered. According to a still further aspect, the invention provides a method for treating or preventing the progression of ALS by administering a therapeutically effective amount of a TAT-BH4 peptide, wherein the TAT-BH4 peptide is in a composition further comprising a pharmaceutically acceptable excipient. The TAT-BH4 peptide can be administered to subjects in need thereof in the form of a composition further comprising an excipient. The term "excipient" as used herein describes a material that does not cause significant irritation to an organism and does not abrogate the biological activity and properties of the composition of the described invention. Excipients must be of sufficiently high purity and of sufficiently low toxicity to render them suitable for administration to a subject being treated. The excipient can be inert, or it can possess pharmaceutical benefits. According to a still further aspect, the invention provides a method for treating or preventing the progression of ALS by administering a therapeutically effective amount of a TAT-BH4 peptide, wherein the composition further comprises at least one additional active ingredient.

The TAT-BH4 peptide can be administered along with an excipient in a composition. The composition can be a pharmaceutical composition.

The term "pharmaceutical composition" is used herein to refer to a composition that is employed to prevent, reduce in intensity, cure or otherwise treat a target condition or disease.

The TAT-BH4 peptide can be from any source, but in some embodiments is the TAT-BH4 according to SEQ ID NO:1 or an active variant or fragment thereof. Thus, in some embodiments, the TAT-BH4 peptide has an amino acid sequence having at least 70% sequence identity to SEQ ID NO: 1.

The methods according to the present invention are illustrated and demonstrated in the Examples described herein.

EXAMPLES

Example 1

Aberrant Expression of mGluR5 in ALS Tissues

A degenerative process of the astrocytes that spatially and temporally correlates with the progression of ALS disease was previously identified in the spinal cord of hSOD1$^{G93A}$ mice. Degenerating astroglial cells were morphologically characterized by an unusually thick and spheroidal cap of glial fibrillary acidic protein (GFAP) (FIG. 1A, hSOD1$^{G93A}$, 100d), which was associated with rare GFAP-positive processes and resulted immunopositive for the active caspase-3. Neuropathological analyses of autoptic tissues from patients affected by sporadic ALS confirmed that these unusual GFAP- and active caspase-3-positive cellular profiles are present in the neighborhood of motor neurons also in the ventral horns of the spinal cord from sALS cases (FIG. 1C-D), thus corroborating the relevance of this phenomenon in the context of the human disease. Because a role for mGluR5 was originally identified in the gliodegenerative process, the authors investigated the expression of the receptor messenger RNA (mRNA) in the spinal cord of hSOD1$^{G93A}$ ALS mice and wild-type control animals at different ages during disease progression. Quantitative reverse transcription-polymerase chain reaction (qRT-PCR) analysis revealed that, at the pre-symptomatic age of 30 days, the mGluR5 mRNA is up-regulated in hSOD1$^{G93A}$ mice when compared to age-matched wild-type animals. However, its levels significantly decrease at the time of disease onset, i.e. about 100 days of age, when the degree of expression becomes comparable with that in wild-type mice (FIG. 1B). The distribution of the receptor was subsequently explored in situ in mGluR5-immunolabelled spinal cord sections from hSOD1$^{G93A}$ and wild-type animals. In both instances, the authors found that, at the age of 30 days, mGluR5 shows the typical punctuate staining of receptor clusters throughout lumbar spinal cord sections, in both neuronal and glial cells (FIG. 1A). However, quantitative analysis of mGluR5-immunofluorescent puncta confirmed a generally enhanced expression of the receptor in hSOD1$^{G93A}$ mice when compared to wild-type animals (mGluR5 expression level in wild-type mouse spinal cord was set as 100%; mGluR5 expression in 30 day-old hSOD1$^{G93A}$ mouse spinal cord: 142±6.6% vs wild type; n=6 fields from 3 mice; p<0.002, paired t-test; FIG. 1A). Because at this phase of the disease the degree of expression of the astrocytic and microglial markers, GFAP and CD11 b, was similar in the two genotypes (GFAP expression level in wild-type mouse spinal cord was set as 100%; GFAP expression in 30 day-old hSOD1$^{G93A}$ mouse spinal cord: 75±13% vs wild type; n=6 fields from 3 mice; p=0.27, paired t-test; CD11b: 102±15% versus wild-type, p=0.12, unpaired t-test, n=6 fields from three mice), the authors suggested that the increase in mGluR5 levels is independent on hyperproliferation of reactive glia. Rather, it is a consequence of the presence of mutant SOD1 in the different cell types. Interestingly, immunohistochemical analyses of hSOD1$^{G93A}$ spinal cords, taken at the time of disease onset, confirmed a widespread expression of mGluR5, which was quantitatively comparable with wild-type spinal cords (79.6±4.1% vs wild-type; n=6 fields from 3 mice; p=0.084, paired t-test). Yet, at this stage of the disease, degenerating astrocytes were largely represented and emerged from the background by exhibiting an intenser mGluR5 immunoreactivity, which was determined by enhanced and closely adjacent mGluR5-positive puncta, when compared to the neighbouring cells (FIG. 1A, hSOD1$^{G93A}$, 100d). In keeping with these observations, a similar pattern of mGluR5 expression was found also in autoptic sALS spinal cords (FIG. 1D). The fact that mGluR5 is overexpressed in the spinal cord of hSOD1$^{G93A}$ mice at the pre-symptomatic stage of the disease, but not at the time of disease onset, i.e. when degenerating astrocytes manifest, strongly suggests that this receptor plays a crucial role in ALS progression by acting at the early stages of the disease.

Materials and Methods

Transgenic mice. Transgenic mice expressing human SOD1$^{G93A}$ (B6SJL-TgN(SOD1-G93A)1Gur were purchased from The Jackson Laboratories. The colonies were maintained by breeding hemizygote males to wild-type C57Bl6/SJL F1 hybrid females. Offspring were genotyped and used for subsequent studies. Animal procedures were approved by the Italian Ministry of Health.

ALS biopsy material. Autoptic tissues from sALS cases were obtained from the department of Pathology of the Academic Medical Center (University of Amsterdam) and the Netherlands ALS tissue bank. Informed consent was obtained for the use of brain tissue. Tissue was acquired and used in a manner compliant with the Declaration of Helsinki. All autopsies took place within 12 hrs after death. All cases were reviewed independently by two neuropathologists and the diagnosis of ALS was confirmed according to the previously described histopathological criteria.

Tissue preparation and immunohistological analysis. For mouse tissue preparation, the spine was taken and immersed in 4% buffered paraformaldehyde for 24 hrs; spinal cord was extracted, the lumbar tract was removed and either paraffin embedded or cryoprotected in 30% sucrose before freezing. For human tissue preparation, spinal cord was removed and 0.5 cm thick slices were taken from the cervical (C7), thoracic (T4 and T8) and lumbar (L1) levels. Slices were fixed in 10% buffered formalin and embedded in paraffin. Mouse or human spinal cords were sectioned at 5-10 μm and used to perform different immunostainings. On selected sections, the following primary antibodies were used: GFAP (mouse monoclonal antibody, 1:50, Dako), CD11b (rat monoclonal antibody, 1:500, Serotec), mGluR5 (rabbit polyclonal antibody, 1:100, MBL International Corporation); active caspase-3 (rabbit polyclonal antibody, 1:50, Cell Signalling Technology). For active caspase-3 immunostaining, a Tyramide Amplification System kit was used (Perkin Elmer, Inc.). For histopathological analysis, serial sections were either immunostained for GFAP/active caspase-3 or treated with 0.5% cresyl violet (Sigma Aldrich) to detect motor neuron Nissl substance. GFAP/active caspase-3 positive astrocytes and motor neurons were counted for a total of 9 disectors using an unbiased stereologic physical disector technique. Z-axis image stacks (z-step size: 0.5 μm) were collected to generate three-dimensional data sets of spinal cord sections on an MRC 1024 Bio-Rad confocal microscope with a 63× Plan Neofluar NA1, 25 oil-immersion objective in condition of optimal iris diameter as defined by LaserSharp 2000 software. Quantitative analysis of punctuate mGluR5, GFAP or CD11 b stainings was performed on confocal acquired images (1024×1024 pixels) of the spinal cord ventral horns from both wild-type and SOD1$^{G93A}$ animals using ImageJ software (National Institutes of Health). After establishing an intensity threshold, the software calculated the percentage of area occupied by mGluR5, GFAP or CD11b staining by dividing the area of immunopositivity by the total area.

Quantitative RT-PCR. Total RNA was extracted from animal tissues using RNeasy Mini kit (QIAGEN) according to manufacturer's guidelines. One microgram of tissue-extracted total RNA was reverse transcribed using iScript cDNA Synthesis Kit according to manufacturer's instructions (QIAGEN). Two nanograms of the resulting cDNA was analysed by quantitative PCR using the SsoFast EvaGreen Supermix on a CFX96 Real-Time PCR Detection System (BIO-RAD). mGluR5-encoding transcripts were detected using primers 5'-mGluR5-Car (5'-AGCTGTTTTGTCCA-CATAT) and 3'-mGluR5-Car (5'-CCAGAGAGTGTTGAGT-TAG). The housekeeping gene hypoxanthine guanine phosphoribosyl transferase (HPRT) was chosen as a reference and its mRNA was detected using primers 5'-HPRT (5'-TGAAT-CACGTTTGTGTCATTA) and 3'-HPRT (5'-TTCAACT-TGCGCTCATCTTAG).

Example 2

Figure 2:
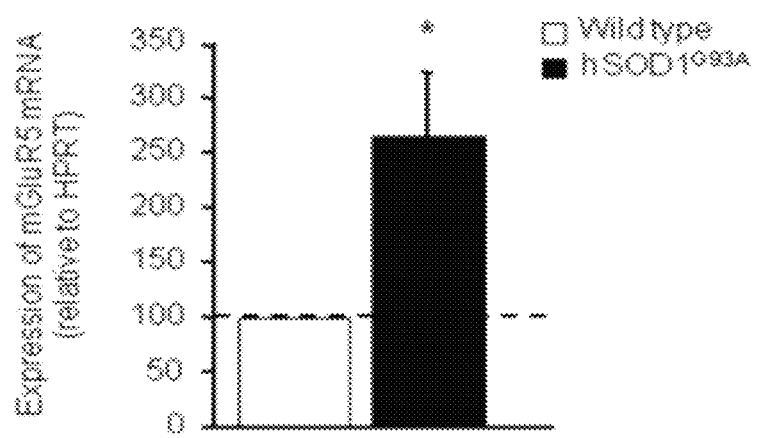
FIG. 2. Impact of $hSOD1^{G93A}$ on mGluR5 expression and DHPG-induced intracellular $Ca^{2+}$ ($[Ca^{2+}]_i$) signalling in astrocytes. (A) Expression of mGluR5 mRNA was determined by qRT-PCR analysis on total RNA from wild-type and hSOD1$^{G93A}$ astrocyte-pure cultures (n=3). Values (mean±s.e.m.) were normalised relative to HPRT and expressed as percentage of mGluR5 expression levels in wild-type cells (*p<0.05 vs wild-type cells, unpaired t-test). (B-D) Local application of the group I metabotropic glutamate receptor (mGluR) agonist (RS)-3,5-dihydroxyphenylglycine (DHPG) induced [Ca$^{2+}$]$_i$ signalling in wild-type and hSOD1$^{G93A}$ cultured astrocytes. (B) Typical single cell [Ca$^{2+}$]$_i$ transients obtained in response to 100 μM of DHPG in three wild-type astrocytes. Note that the majority of cells (67.7±1.23%; n=93 cells analyzed; n=7 experiments) responded with a single [Ca$^{2+}$]$_i$ transient (ΔF/F$_0$ 0.27±0.18) followed by sustained [Ca$^{2+}$]$_i$ oscillations (average frequency 17±2.5 mHz). (C) As in (B) but in hSOD1$^{G93A}$ astrocytes. Note that contrary to wild-type astrocytes, the majority of hSOD1$^{G93A}$-expressing cells (99±2.5%; n=84 cells analyzed; n=6 experiments) responded to DHPG with a reduced single [Ca$^{2+}$]$_i$ transient (−63%; ΔF/F$_0$ 0.1±0.08) followed by an abnormal long-lasting calcium rise that reaches the plateau in about 10 min. (ΔF/F$_0$ 0.55±0.3). (D) Summary (mean±s.e.m.) of >50 cells in multiple trials representing peak amplitude of initial DHPG-evoked [Ca$^{2+}$]$_i$ transient (expressed as ΔF/F$_0$) (top) and percentage of cells responding with oscillations (bottom) (*p<0.001, paired t-test vs wild-type cells).

Altered mGluR5-Mediated Intracellular Calcium ([Ca$^{2+}$]$_i$) signalling in hSOD1$^{G93A}$-Expressing Astrocytes is Coupled to Cell Death To determine whether the global over-expression of mGluR5 identified in the spinal cord of young ALS mice was reflected on astrocytes, the authors switched to studies in cell culture. First, they quantified the levels of the receptor mRNA in primary astrocytes deriving from the spinal cord of newborn hSOD1$^{G93A}$ and wild-type animals. qRT-PCR analysis revealed that hSOD1$^{G93A}$-expressing astrocytes show a 2.6-fold increase in the amount of mGluR5 transcripts when compared to wild-type sister cultures (FIG. 2A). The mGluR5 Ca$^{2+}$-signalling was then studied by single-cell Fluo4 imaging of the [Ca$^{2+}$]$_i$ changes induced by (RS)-3,5-dihydroxyphenylglycine (DHPG), a selective agonist of group I mGluRs. They found that the majority of wild-type astrocytes (about 68%, FIG. 2D) responded to the local application of 100 μM DHPG with a single [Ca$^{2+}$]$_i$ transient followed by sustained [Ca$^{2+}$]$_i$ oscillations (FIGS. 2B and D). In hSOD1$^{G93A}$-expressing astrocytes, the [Ca$^{2+}$]$_i$ signalling features were completely different; almost all astrocytes challenged with DHPG (about 99%) displayed a decreased initial [Ca$^{2+}$]$_i$ transient (−63% of ΔF/F$_0$ with respect to wild-type cells, FIGS. 2C and D), followed by a secondary long-lasting rise in cytosolic [Ca$^{2+}$]$_i$ reaching the plateau level in about 10 min. The amplitude of the [Ca$^{2+}$]$_i$ plateau was slightly heterogeneous, ranging from 0.25 to 0.8 ΔF/F$_0$, and this pattern was associated to the lack of oscillatory [Ca$^{2+}$]$_i$ signals (FIG. 2C). Since prolonged [Ca$^{2+}$]$_i$ overload can activate a variety of signalling cascades that lead to cell death, the authors hypothesized that the unusual efflux of intracellular Ca$^{2+}$ detected in the mutant SOD1-expressing cells, in combination with the loss of IP$_3$R-dependent [Ca$^{2+}$]$_i$ oscillations, may underlie degeneration of ALS astrocytes. In keeping, they confirmed that the same concentration of DHPG triggers the release of cytochrome c from mitochondria (FIG. 4A and Example 4). This event is associated with delayed (24 hrs) caspase-3 activation and nuclear condensation in a subset of mutant SOD1-expressing astrocytes (FIG. 4B and Example 4). Because mGluR5, but not the closely related mGluR1, is expressed in cultured astrocytes, the authors conclude that the effects elicited by DHPG in ALS astroglial cells can be ascribed to mGluR5 activation.

Materials and Methods

Astrocytes cultures. Primary astrocyte cultures (>99% GFAP-positive) were prepared from the spinal cord of newborn mice (hSOD1$^{G93A}$ or wild-type littermates). Once the cultures reached the confluence, they were replated at the optimal density either in 24-well plates or 35-mm Petri dishes containing glass coverslips and maintained in Minimal Essential Medium (MEM, GIBCO) supplemented with 10% foetal bovine serum (FBS, Sigma-Aldrich).

Quantitative RT-PCR. Total RNA was extracted from confluent astrocytes in culture using RNeasy Mini kit (QIAGEN) according to manufacturer's guidelines. One microgram of astrocyte-extracted total RNA was reverse transcribed using iScript cDNA Synthesis Kit according to manufacturer's instructions (QIAGEN). Two nanograms of the resulting cDNA was analysed by quantitative PCR using the SsoFast EvaGreen Supermix on a CFX96 Real-Time PCR Detection System (BIO-RAD). mGluR5-encoding transcripts were detected using primers 5'-mGluR5-Car (5'-AGCT-GTTTTGTCCACATAT) and 3'-mGluR5-Car (5'-CCA-GAGAGTGTTG AGTTAG). The housekeeping gene HPRT was chosen as a reference and its mRNA was detected using primers 5'-HPRT (5'-TGAATCACGTTTGTGTCATTA) and 3'-HPRT (5'-TTCAACTTGCGCTCATCTTAG).

$[Ca^{2+}]_i$ imaging. ASTROCYTES were plated ($2.5 \times 10^4$ cells/35 mm Petri dish) on glass coverslips and used 2-3 days later as already shown. Before imaging, cells were loaded with 5 µM Fluo4-AM (Molecular Probes) for 15-20 min. at 37° C. in a HEPES-KRH buffer containing (in mM): NaCl 116, KCl 4, $MgCl_2$ 1, $CaCl_2$ 1.8, HEPES-acid 10, glucose 25 (pH 7.4) and then allowed to de-esterify for 10 min. After several washes, coverslips were mounted in an open perfusion micro-incubator (PDMI-2, Harvard Apparatus) set at 37° C. on the stage of the optical recording microscope. During experiments, cells were continuously perfused with HEPES-KRH (1 ml/min), and 100 µM DHPG was applied via a software-controlled micro-perfusion fast-step device (100 µl/min, Warner Instrument Corp.) A Zeiss Axiovert 200 inverted fluorescence microscope was modified to allow EPI illumination (Visitron Systems). Fluo4 fluorescence was recorded through a 63× or 40× objectives lens (Zeiss, Neofluar 63×/1.25 Oil, Neofluar 40×/1.3 Oil) and directed through a Zeiss filter set 10 (BP 450-490; BP 515-565) at 200- or 400 ms of intervals by imaging with excitation light at 488 nm generated by a polychromator illumination system (Visichrome, Visitron). Video images, digitized with MetaFluor, were analyzed with MetaMorph software (Universal Imaging). Temporal dynamics of Fluo4 fluorescence have been expressed as background-subtracted $\Delta F/F_0 (\%)$, where $F_0$ represents the fluorescence level of the cells before stimulation, and F represents the change in fluorescence occurring during the stimulus.

Example 3

Figure 3:
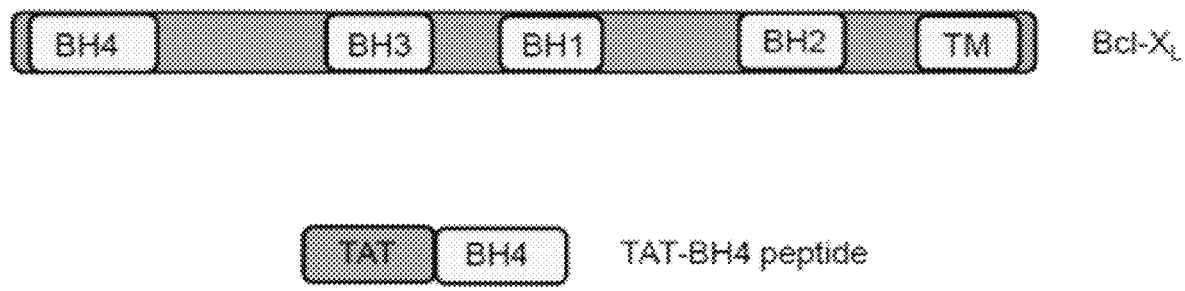
FIG. 3. The TAT-BH4 peptide restores normal spontaneous and DHPG-evoked [Ca$^{2+}$]$_i$ signalling in hSOD1$^{G93A}$-expressing astrocytes. (A) Schematic representation of both the full-length Bcl-X$_L$ protein with its four Bcl-2 Homology (BH) domains and the C-terminal hydrophobic domain (TM) and the TAT-BH4 peptide. (B) TAT-BH4 is internalized into primary astrocytes in culture. Cultured cells were stained with the nuclear dye Hoechst 33342, quickly washed and incubated in the presence of 0.5 μM unconjugated (TAT-BH4, control) or 5(6)-carboxyfluorescein (FAM)-conjugated TAT-BH4 (TAT-BH4-FAM). Peptides in excess were subsequently removed and cells were immediately fixed (acute) or maintained in culture for 24 hrs and then fixed (24 hrs). While cells treated with unconjugated TAT-BH4 (control) exhibit only the nuclear staining, those incubated with TAT-BH4-FAM show the presence of the fluorescent marker in about all astrocytes even 24 hrs after the removal of the peptide from the cell culture media. Scale bar, 20 μm. (C) Representative single cell [Ca$^{2+}$]$_i$ transients obtained in three hSOD1$^{G93A}$-expressing astrocytes treated with TAT-BH4 peptide (0.5 μM; grey traces) for 30 min. before the local application of DHPG (100 μM; black traces). Note that in the presence of TAT-BH4 in 100% of hSOD1$^{G93A}$ expressing astrocytes (n=90 cells analyzed; n=8 experiments), DHPG-evoked [Ca$^{2+}$]$_i$ transients show a pattern similar to that obtained in wild-type astrocytes (FIG. 2B): black traces show a single [Ca$^{2+}$]$_i$ transient followed by sustained [Ca$^{2+}$]$_i$ oscillations (average frequency 14±3.1 mHz). (D) Summary (mean±s.e.m.) of >50 cells in multiple trials representing the percentage of cells responding with oscillations (top) and the average oscillation frequency (bottom) per each genotype and treatment (*p<0.01 vs TAT-BH4 in wild-type and TAT-BH4 in hSOD1$^{393A}$, one-way ANOVA followed by Bonferroni post-hoc test).
Figure 3B:
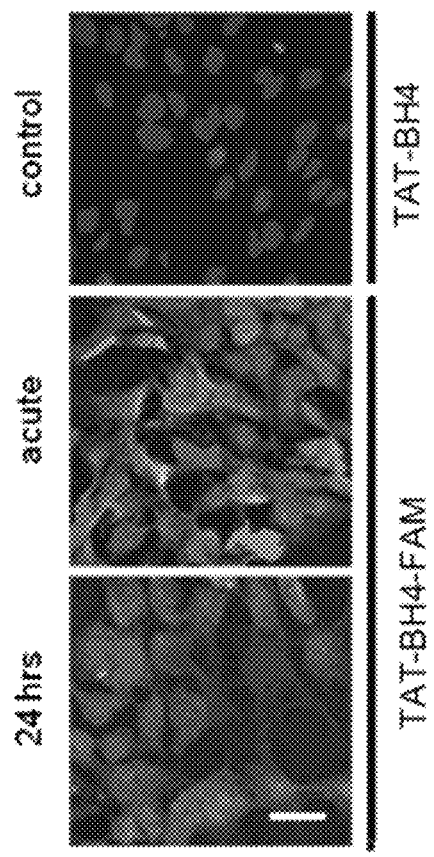

The BH4 Domain of $Bcl-X_L$ Restores $[Ca^{2+}]_i$ Oscillations in $hSOD1^{G93A}$-Expressing Astrocytes Several lines of evidence indicate that the members of the Bcl-2 family are important regulators of cell death mechanisms, and this has been attributed, at least in part, to their ability to modulate endoplasmic reticulum (ER) $Ca^{2+}$ signals. Notably, $Bcl-X_L$ was reported to exert its full anti-apoptotic effects by directly binding to the $IP_3Rs$. This interaction was shown to sensitize cells to low concentrations of $IP_3$ and enhance spontaneous $[Ca^{2+}]_i$ oscillations, an event that has been correlated with increased cell death resistance. However, the specific domain of $Bcl-X_L$ involved in this process was not elucidated. Since the BH4 domain of $Bcl-X_L$ importantly contributes to cell death suppression, the authors of the present invention decided to test the effects towards $[Ca^{2+}]_i$ signalling of TAT-BH4, a fusion peptide in which BH4 is conjugated with the cell-penetrating TAT peptide from the HIV-1 virus (FIG. 3A). To determine whether TAT-BH4 is transduced into primary astrocytes and to assess its stability inside the cells over time, they first incubated cultured astroglial cells with either unconjugated or 5(6)-carboxyfluorescein (FAM)-conjugated TAT-BH4 (TAT-BH4-FAM, 0.5 µM, 30 min.) (FIG. 3B). Cells were subsequently washed and either immediately fixed or maintained in culture for 24 hrs and then fixed, according to the timing of our toxicity experiments. The presence of TAT-BH4-FAM into nearly 100% of astrocytes was confirmed by fluorescence microscopy. Noteworthy, significant levels of the transduced fluorescent marker persisted in the astrocytes even 24 hrs after the removal of the peptide from the cell culture media (FIG. 3B). Then, we tested the efficacy of TAT-BH4 in regulating DHPG-induced $[Ca^{2+}]_i$ signalling in mutant SOD1-expressing astrocytes. Calcium imaging experiments were first carried out by challenging Fluo4-loaded wild-type and $hSOD1^{G93A}$-expressing astrocytes with TAT-BH4 (0.5 µM, 30 min.). Surprisingly, the authors found that the local application of TAT-conjugated BH4 caused an immediate $[Ca^{2+}]_i$ rise followed by sustained $[Ca^{2+}]_i$ oscillations in cells of both genotypes (FIGS. 3C and D). In $hSOD1^{G93A}$-expressing astrocytes, administration of the mGluR agonist DHPG (100 µM), 30 min. after the application of TAT-BH4, triggered the typical single $[Ca^{2+}]_i$ transient in 99% of the cells, followed by persistent $[Ca^{2+}]_i$ oscillations. The average oscillation frequency was similar to that of wild-type cells (FIGS. 3C and D). Thus, based on these observations, the authors conclude that the BH4 domain of $Bcl-X_L$ is sufficient to abolish unregulated $[Ca^{2+}]_i$ rises and to restore both spontaneous and evoked $[Ca^{2+}]_i$ oscillations in ALS astrocytes.

Materials and Methods $[Ca^{2+}]_i$ imaging. The measurements of $[Ca^{2+}]_i$ were performed as described in Example 2. Briefly, cells were loaded with 5 µM Fluo4-AM and then allowed to de-esterify for 10 min.

After several washes, coverslips were mounted in an open perfusion micro-incubator set at 37° C. on the stage of the optical recording microscope. During experiments, cells were continuously perfused with HEPES-KRH (1 ml/min), and 0.5 µM TAT-BH4 was applied 30 min. before adding 100 µM DHPG via a software-controlled micro-perfusion fast-step device (100 µl/min, Warner Instrument Corp.).

Example 4

TAT-BH4 Protects Astrocytes from $IP_3R$-Driven Toxicity by Fine-Tuning $[Ca^{2+}]_i$ Signalling In the next set of experiments, the authors evaluated whether the restoration of $[Ca^{2+}]_i$ oscillations in $hSOD1^{G93A}$-expressing astrocytes correlated with a glioprotective effect of TAT-BH4 against mGluR5-dependent excitotoxic damage. Spinal astrocytic cultures from $hSOD1^{G93A}$ or wild-type mice were pre-incubated in the absence or in the presence of 0.5 µM TAT-BH4 for 30 min. The peptide in excess was then removed and cells were exposed to 100 µM DHPG or control solution (30 min.). In the absence of TAT-BH4, they confirmed that DHPG induces the release of cytochrome c from mitochondria (FIG. 4A), an event that is associated to caspase-3 activation and nuclear condensation selectively in mutant SOD1-expressing astrocytes, but not in the wild-type counterpart (FIG. 4B). However, when astrocytes deriving from $hSOD1^{G93A}$ mice were pre-treated with the TAT-BH4 peptide, a significant reduction in both the release of cytochrome c and the apoptotic parameters was detected (FIG. 4A-B). To ascertain whether the identified alterations in intracellular $Ca^{2+}$ signalling strictly correlated with the mGluR5- dependent gliodegenerative process, the authors subsequently performed single-cell $[Ca^{2+}]_i$ imaging of wild-type astrocytes stimulated with staurosporine (STS), a well-established pro-apoptotic stimulus that leads to cell death by causing $Ca^{2+}$ leak from the intracellular stores via the activation of $IP_3Rs$. Similarly to DHPG-stimulated ALS astrocytes, they found that STS (1 μM) triggers a persistent increase in cytosolic calcium that reaches the plateau in about 75-80 min. This event is coupled to the absence of evident calcium oscillations (FIG. 4C). However, when STS was administered 30 min. after the application of TAT-BH4, the authors observed a significant reduction in the levels of intracellular calcium (−72% with respect to cells treated with STS alone), coupled to the re-establishment of $[Ca^{2+}]_i$ oscillations (FIG. 4D). Interestingly, the variations in $[Ca^{2+}]_i$ occurring in the absence or in the presence of TAT-BH4 quantitatively correlated with astrocyte degeneration. Indeed, in parallel experiments, they found that treating astrocytes with STS (1 μM) in the absence of the peptide induced cell death, as determined by nuclear condensation (FIG. 4E). However, when cells were pre-incubated with increasing concentrations of TAT-BH4 (0.1 and 0.5 μM, 30 min.), astrocyte degeneration was potently inhibited in a dose-dependent fashion (FIG. 4E). In view of the impact of STS on $IP_3Rs$, the authors conclude that astroglial transduction of TAT-BH4 is effective in protecting the cells against $IP_3R$-driven cell death.

Materials and Methods

Pharmacological treatments in vitro. To assess the ability of TAT-BH4 to penetrate into cells, astrocytes ($8 \times 10^4$ cells/well) were plated in 24-well plates containing glass coverslips. Cultures were treated with 10 μg/ml Hoechst 33342 (Sigma) for 15 min., quickly washed and incubated with 0.5 μM TAT-BH4 ($TAT^{48-57}$ conjugated to the BH4 domain of $Bcl-X_L$) either unconjugated or conjugated with 5(6)-carboxyfluorescein (FAM, Primm srl) for 30 min. Peptides in excess were subsequently removed, cells were washed and immediately fixed (methanol:acetone 1:1 for 10 min.) or maintained in culture for 24 hrs and then fixed. The presence of the peptides inside the cells was evaluated by a digital camera (DFC 310 FX, Leica Microsystem) mounted on a DM5000 B microscope (Leica Microsystem) and analysed by Leica Application Suite 3.5.0 software. To test the protective efficacy of TAT-BH4, astrocytes in culture were pre-exposed to different concentrations of the peptide (0.1 and/or 0.5 μM, 30 min.), washed and then treated with DHPG (100 μM, 30 min., Tocris Cookson Ltd.) or staurosporine (1 μM, 6 hrs, Sigma-Aldrich). After removal of DHPG, astrocytes were allowed to recover at 37° C. for 24 hrs.

Astrocyte toxicity assays. The toxic effect of DHPG or staurosporine on cultured astrocytes was determined by double staining with the fluorescent nuclear dye Hoechst 33342 and anti-active caspase-3 immunocytochemistry using a rabbit polyclonal antibody (1:50, Cell Signalling Technology). The number of astrocytes showing condensed nuclei and activated caspase-3 24 hrs after the pharmacological challenge was counted by two independent operators in a blind manner. The number of dying astrocytes was counted in 8 to 10 microscopic fields (40×) per coverslip and expressed as percentage of the total number of cells present in the field.

Cytochrome c release. Confluent astrocytes were fixed either in 4% buffered paraformaldehyde for 15 min at room temperature. Cells were then immunostained using the following primary antibodies: cytochrome c (mouse monoclonal antibody, 1:100, BD Pharmingen), SOD2 (rabbit polyclonal antibody, 1:50, Stressgen). Cytochrome c release from mitochondria was determined by its co-localization with the mitochondrial protein SOD2 using JACoP plug-in ImageJ. An estimate of the degree of co-localization was obtained by calculating the Pearson's and Manders' coefficients.

Example 5

In vivo Administration of TAT-BH4 Reduces Astrocyte Degeneration, Slightly Postpones Disease Onset and Improves Both Motor Performance and Survival of $hSOD1^{G93A}$ Mice Based on the above observations, the authors decided to assess the therapeutic potential of TAT-BH4 in vivo on ALS transgenic mice. Starting at the age of 40 days, $hSOD1^{G93A}$ animals were treated daily with TAT-BH4 (5 mg/kg in phosphate buffered saline (PBS) containing 10% glycerol, intraperitoneally) or equivalent volumes of vehicle solution (PBS plus 10% glycerol, control). Thereafter, mice were monitored daily for survival and twice a week for both decline in body weight and motor performance using the rotarod test. As weight gain stops at the time of disease onset, the peak in the body weight curve was taken as the earliest measure of the onset of the disease. According to this criterion, the authors found that the disease manifestation was slightly, but significantly, delayed in mice injected with TAT-BH4 compared with controls (saline: 99.1±2.9 days; TAT-BH4: 107.5±1.8 days, n=14 per experimental group; p<0.05, Logrank test; FIG. 5A). In addition, mice treated with TAT-BH4 performed significantly better in the rotarod tasks throughout life (FIG. 5B) and had a prolonged survival time compared with vehicle-injected mice (saline: 123±2.1 days; TAT-BH4: 138±2.1 days, n=14 per experimental group; p<0.001, Logrank test; FIG. 5C). On the basis of these findings, they conclude that the treatment with TAT-BH4 slightly delays the onset of the disease, slows the rate of disease progression and reduces degeneration of astrocytes and motor neurons.

To determine whether the positive effect of the peptide on disease onset and progression was related to the identified degenerative process of astrocytes, the authors next investigated the impact of TAT-BH4 on both glial and neuronal cells. They found that the treatment with the peptide significantly reduced the number of spheroid astrocytes immunopositive for the active caspase-3 located in the motor neuron microenvironment (−74% with respect to saline-treated mice, FIG. 5D), but not the overall number of GFAP-positive astrocytes distributed throughout the spinal ventral horns (saline: 987.7±29.1 cells/mm$^2$; TAT-BH4: 917.9±33.1 cells/mm$^2$; n=18 fields from three mice; p=0.07, unpaired t-test). Noteworthy, the quantity of CD11b-immunopositive microglial cells were slightly, but significantly, decreased upon chronic injection of TAT-BH4 (saline: 1194±20 cells/mm$^2$; TAT-BH4: 1040.7±20.4 cells/mm$^2$; n=18 fields from three mice; p<0.05, unpaired t-test). This result correlated with the preservation of a greater number of motor neurons (FIG. 5E). On the basis of these findings, it was concluded that the treatment with TAT-BH4 slightly delays the onset of the disease, slows the rate of disease progression and reduces degeneration of astrocytes and motor neurons.

Materials and Methods

Pharmacological treatment in vivo. $hSOD1^{G93A}$ mice were administrated daily 5 mg/kg TAT-BH4 peptide in PBS containing 10% glycerol or vehicle alone (PBS plus 10% glycerol) intraperitoneally starting at the age of 40 days (n=14 mice for each condition). Mice were thereafter kept under daily observation and weighted twice a week. Age of disease onset was retrospectively determined as the time when mice reached the peak in the body weight. Motor performance was assessed twice a week by rotarod test starting at the age of 50 days. Briefly, animals were place on an accelerating rod (Ugo Basile) and the time each mouse remained on the rod was recorded. The average of three independent trials per session was used for further analysis of the data. End stage was defined as the time in which animals were unable to right themselves within 30 seconds when placed on their side.

Statistics. Data are represented as mean±s.e.m. and statistical significance is verified using GraphPad Prism software. Unpaired or paired 2-tailed t-test was used for comparisons between two groups; one-way or two-way analysis of variance (ANOVA) followed by Bonferroni post-hoc test was used for comparisons of multiple groups; repeated measures two-way ANOVA was used for behavioral test; the Logrank test was used for disease onset and survival analysis.

From the above description and the above-noted Examples, the advantages attained by the methods for treating and preventing the progression of ALS described and obtained according to the present invention are apparent. While the present invention has been described with reference to the specific embodiments thereof it should be understood by those skilled in the art that various changes may be made and equivalents may be substituted without departing from the true spirit and scope of the invention. In addition, many modifications may be made to adopt a particular situation to the objective spirit and scope of the present invention. All such modifications are intended to be within the scope of the claims appended hereto. Although specific terms are employed herein, they are used in a generic and descriptive sense only and not for purposes of limitation.

The invention claimed is:

1. A method for treating or preventing the progression of ALS, the method comprising administering a TAT-BH4 peptide to a subject in need thereof, wherein the TAT-BH4 peptide has the amino acid sequence set forth in SEQ ID NO: 1.

2. The method of claim 1, wherein at least one manifestation or symptom of ALS is treated or prevented.

3. The method of claim 2, wherein said at least one manifestation or symptom of ALS is chosen from the group comprising muscle weakness and atrophy.

4. The method of claim 1, wherein the TAT-BH4 peptide promotes cell-death resistance.

5. The method of claim 4, wherein the cells that resist cell-death are chosen from the group consisting of astroglial cells and motor neurons.

6. The method of claim 1, wherein the TAT-BH4 peptide enhances cell survival by restoring $Ca^{2+}$ oscillations.

7. The method of claim 1, wherein the TAT-BH4 peptide reduces the degeneration of spinal cord astrocytes.

8. The method of claim 1, wherein the TAT-BH4 peptide postpones the appearance of ALS symptoms.

9. The method of claim 1, wherein the TAT-BH4 peptide improves motor performance and survival.

10. The method of claim 1, wherein the TAT-BH4 peptide is a glioprotective agent.

11. The method of claim 1, wherein the TAT-BH4 peptide is intraperitoneally administered.

12. The method of claim 11, wherein the TAT-BH4 peptide is chronically administered.

13. The method of claim 1, wherein the TAT-BH4 peptide is in a composition further comprising a pharmaceutically acceptable excipient.

14. The method of claim 13, wherein the composition further comprises at least one additional active ingredient.

* * * * *